(12) United States Patent
Gonzalez et al.

(10) Patent No.: US 7,402,437 B2
(45) Date of Patent: Jul. 22, 2008

(54) METHOD AND DEVICE FOR ANALYZING THE INTRACELLULAR CHEMICAL STATE OF LIVING CELLS BY NUCLEAR MAGNETIC RESONANCE

(75) Inventors: Benjamin Gonzalez, Clermond-Ferrand (FR); Martial Piotto, Oswald (FR); J. Gaspard Huber, Brive la Gaillarde (FR)

(73) Assignee: Bruker Biospin S.A., Wissembourg (FR)

( * ) Notice: Subject to any disclaimer, the term of this patent is extended or adjusted under 35 U.S.C. 154(b) by 948 days.

(21) Appl. No.: 10/398,942

(22) PCT Filed: Oct. 12, 2001

(86) PCT No.: PCT/FR01/03167

§ 371 (c)(1),
(2), (4) Date: May 19, 2003

(87) PCT Pub. No.: WO02/31523

PCT Pub. Date: Apr. 18, 2002

(65) Prior Publication Data

US 2003/0199751 A1    Oct. 23, 2003

(30) Foreign Application Priority Data

Oct. 13, 2000    (FR) .................................. 00 13183

(51) Int. Cl.
*G01N 24/00*    (2006.01)
*G01V 3/00*     (2006.01)

(52) U.S. Cl. ....................... 436/173; 324/307; 324/309; 324/317

(58) Field of Classification Search ................... 436/56
See application file for complete search history.

(56) References Cited

U.S. PATENT DOCUMENTS 5,851,999 A  * 12/1998 Ullrich et al. .................. 514/44
2002/0135365 A1 * 9/2002 Wind et al. .................. 324/307

FOREIGN PATENT DOCUMENTS

WO    WO 92 01946 A    2/1992

OTHER PUBLICATIONS

Valentine et al. "Structure, Topology, and Dynamics of Myristoylated Recoverin Bound to Phospholipid Bilayers", Biochemistry, 2003, v. 42, No. 21, pp. 6333-6340.*
Tong et al. "Structure and Dynamics of Pentaglycyl Bridges in the Cell Walls . . . ", Biochemistry, 1997, v. 36, pp. 9859-9866.*

(Continued)

Primary Examiner—Yelena G. Gakh
(74) Attorney, Agent, or Firm—Foley & Lardner LLP

(57) ABSTRACT

The invention concerns a method for analysing the intracellular chemical state of living cells by nuclear magnetic resonance (NMR). Said method comprises a step which consists in preparing the cell sample and a step which consists in an NMR analysis of the sample, both steps being carried out at very low temperature so as to freeze the biochemical state of the living cells to obtain specific and accurate reproducible measurements of the cellular functioning in given conditions. The invention also concerns the device coupled to the NMR spectrometer for implementing the method of analysis.

15 Claims, 5 Drawing Sheets

OTHER PUBLICATIONS

Figure 1:
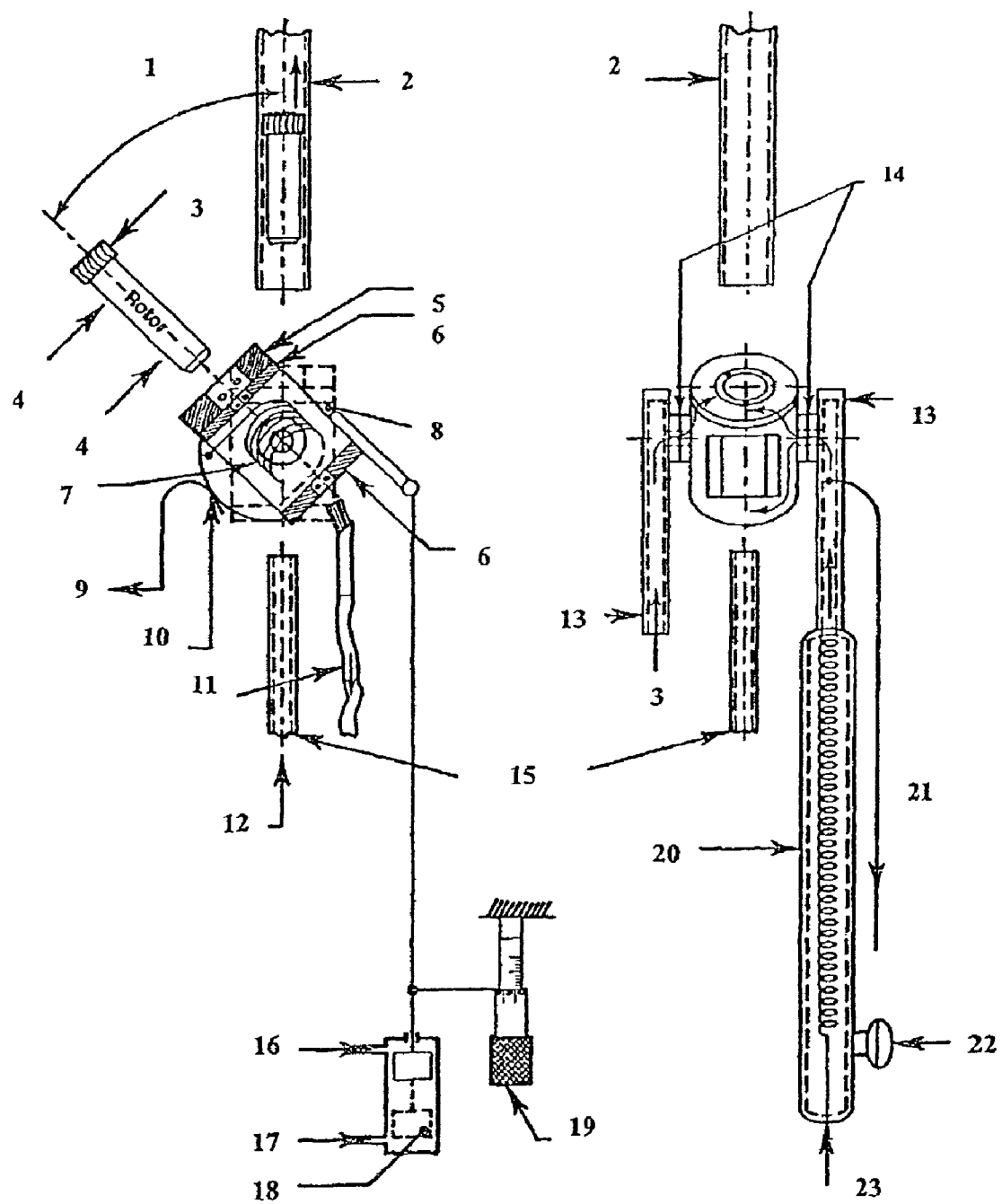

Hahn et al. "Recovery and Characterization of Poly(3-Hydroxybutyric Acid . . ." Applied and Environmental Microbiology, 1995, pp. 34-39.*

Schaefer et al. "Characterization of peptidoglycan stem lengths by soid-state 13C and 15N NMR", Biochem. Biophjys. Res. Commun., 1986, v. 137, No. 2, pp. 736-741, Abstract.*

Hacob et al. "Solid-state carbon-13 and nitrogen-15 nuclear magnetic resonance studies of alanine metabolism in Aerococcus viridans (Gaffkya homari)", Journal of Biological Chemistry,1985, 260(5), 2777-81, Abstract.*

Wilson et al. "Solid state nitrogen-15 NMR studies of the effects of penicillin on cell wall metabolism of Aerococcus viridans (Gaffkya homari)", Biochemical and Biophysical Research Communications, 1985, 126(3), 1006-12, Abstract.*

Kono et al. "Nuclear magnetic resonance spectrometric assay of b-lactamase in bacterial cells", Drug Resist. Bact., [Tokyo Symp.], 3rd (1982), Meeting Date 1981, 333-6. Editor(s): Mitsuhashi, Susumu. Japan Sci. Soc. Press: Tokyo, Japan.*

Li, W. "Multidimensional HRMAS NMR: a platform for in vivo studies using intact bacterial cells", Analyst, 2006, 131, pp. 777-781.*

A.H. Fowler et al, "Differentiation of Human Prostate Cancer From Benign Hypertrophy By In Vitro 1H NMR," *Magnetic Resonance in Medicine*, May 1, 1992, pp. 140-147, vol. 25, No. 1, XP000275042, ISSN: 0740-3194, US Academic Press, Duluth, MN.

Bjorn Quistorff et al., "Methods for liquid- and solid-state CP-MAS NMR spectroscopy of untreated tissue biopsies," *Analytical Biochemistry*, pp. 68-74, vol. 213, No. 1, XP001007253, ISSN: 0003-2697, 1993.

W De Koning et al., "A Method for the Determination of Changes of Glycolytic Metabolites in Yeast on a Subsecond Time Scale Using Extraction at Neutral PH," *Analytical Biochemistry*, 1992, pp. 118-123, vol. 204, No. 1, XP001007232, ISSN: 0003-2697.

R.A. Wind et al., "An investigation of rat mamary healthy and R3230AC tumor tissues and cells by means of solid-state / sup 13/C NMR," *Solid State Nuclear Magnetic Resonance*, Dec. 1996, pp. 263-269, vol. 7, No. 3, XP001007010 ISSN: 0926-2040.

L.L. Cheng et al., "Enhanced resolution of proton NMR spectra of malignant lymph nodes using magic-angle spinning," *Magnetic Resonance in Medicine*, Nov. 1996, pp. 653-658, vol. 36, No. 5, XP002170690, ISSN: 0740-3194, Williams & Wilkins, USA.

A.R. Tate et al., "Distinction between normal and renal cell carcinoma kidney cortical biopsy samples using pattern recognition of /sup 1/H magic angle spinning (MAS) NMR spectra," *NMR in Biomedicine*, Apr. 2000, pp. 64-71, vol. 13, No. 2, XP002170691, ISSN: 0952-3480, Wiley, UK.

D.A. Middleton et al., he effect of sample freezing on proton magic-angle spinning NMR spectra of biological tissue, *Magnetic Resonance in Medicine*, Jul. 1998, pp. 166-169, vol. 40, No. 1, XP002170692, ISSN: 0740-3194.

N.J. Waters et al, "High-resolution magic angle spinning 1H NMR spectroscopy of intact live and kidney: Optimization of sample preparation procedures and biochemical stability of tissue during spectral acquisition," *Analytical Biochemistry*, Jun. 15, 2000, pp. 16-23, vol. 282, No. 1, XP002170693, ISSN: 0003-2697.

Hanaoka Hideto, "In Vitro Characterization of Lung Cancers by the Use of 1H Nuclear Magnetic Resonance Spectroscopy of Tissue Extracts and Discriminant Factor Analysis," Apr. 1, 1993, pp. 436-440, vol. 29, No. 4, XP000368010, ISSN: 0740-3194.

P.J. Allen et al., "Apparatus for Low-Temperature Magic-Angle Spinning NMR" *Journal of Magnetic Resonance*, May 1, 1991, pp. 614-617, vol. 92, No. 3, XP000203289, ISSN: 1090-7807.

Guy Lippens et al., "Study of Compounds Attached to Solid Supports Using High Resolution Magic Angle Spinning NMR," Analytical Methods in Organic Chemistry, Current Organic Chemistry, vol. 3, No. 2, Mar. 1999, Contents, Aim and Scope, pp. 147-169.

* cited by examiner

METHOD AND DEVICE FOR ANALYZING THE INTRACELLULAR CHEMICAL STATE OF LIVING CELLS BY NUCLEAR MAGNETIC RESONANCE

The present invention relates to a noninvasive method for analyzing intracellular metabolism in vivo. The method uses nuclear magnetic resonance (NMR) to measure the intracellular chemical state of animal or plant cells or microorganisms cultured under defined and controlled conditions.

The invention relates in particular to a method for analyzing the intracellular chemical state of living cells by NMR, which comprises a step of preparing the sample of cells and a step of analyzing the sample by NMR, carried out at very low temperatures in order to fix the biological state of the living cells so as to have reproducible, specific and true measurements of cellular function under given conditions. The invention also relates to the device coupled to the NMR spectrometer for carrying out the method of analysis.

Intracellular concentrations are fundamental parameters for characterizing and correlating the influence of genetic and environmental modifications on the function of the cell (Weuster-Botz et al., 1966; Teusink et al., 1998). By measuring intracellular concentrations, it is possible to determine a metabolic profile specific for the living organism cultured under standard conditions and to compare this profile to those obtained after genetic modifications or after various culture conditions.

Techniques dedicated to determine intracellular parameters in vivo are divided up into two groups: invasive methods and noninvasive methods.

Invasive methods require destruction of the cells and extraction of the intracellular chemical compounds. These two steps take place under extreme physicochemical conditions. Consequently, it is common to find in the literature contradictory data for the intracellular concentrations of the same organism cultured under the same conditions (Gancedo et al., 1973; Weuster-Botz et al., 1996; Gonzalez et al., 1997).

Noninvasive methods, such as nuclear magnetic resonance (NMR) have the advantage of characterizing the intracellular chemical state of living cells without disturbing the cell metabolism (Gadian et al., 1983). Many scientific reviews show that this technique is the analytical tool which is best suited to analyzing intracellular metabolism in vivo (Jeffrey et al., 1991; Cameron et al., 1997).

In this context, detection of the chemical state of living systems by NMR has already been proposed. In this regard, mention may be made of international patent application WO 92/01946, which is directed toward a method for measuring the chemical state of animal or human living systems by nuclear magnetic resonance.

While, with this device, it is possible to detect cellular dysfunction on tissues compared to a defined reference on healthy tissues, it is much more difficult to apply it in order to specifically correlate and characterize a cellular function of microorganisms, of animal cells and of plant cells by NMR measurement of the intracellular chemical state. Specifically, the sensitivity of living systems to environmental conditions makes it difficult to apply this device to measuring the intracellular chemical state of cells and especially to specifically correlating this state to the experimental conditions. This was confirmed by Middleton et al. (1998), who showed the influence of the conditions for preparing disease-affected biological tissues on the metabolic profiles obtained by High Resolution Magic Angle Spinning NMR (HR MAS NMR). Through these experiments, they underlined the difficulty in correlating the pathological factors experimentally studied and the metabolic profiles measured with the device mentioned above.

The cause of the difficulties in specifically associating an intracellular profile measured with NMR devices with the experimental conditions lies in the method and the amount of time for preparing and measuring the samples. It is important to underline that the rates of metabolic reactions, and particularly of those involved in energy metabolism, are high; for example, the rate of conversion of intracellular glucose is 1 mmol.$1^{-1}$ $s^{-1}$ and that of ATP (adenosine-triphosphate) is 1.5 mmol. $1^{-1}s^{-1}$ (De Koning and van Dam, 1992; Theobald et al., 1993). The intracellular contents reported in the literature for these two compounds are less than 4 mmol.$1^{-1}$ (Ryll et al., 1991; Seiler et al., 1994). These data show that a sampling time and/or a measuring time of greater than 6 seconds results in considerable variations in the intracellular concentrations.

It is therefore essential, to obtain reproducible and specific NMR measurements of cellular function for a given condition, to maintain the cells in a stable state not only between the time $t_0$, at which the cells are sampled according to the method for culturing the cells, and the time $t_1$, at which the chemical state is measured by nuclear magnetic resonance, but also during the NMR measurement.

The present invention therefore proposes to solve these problems by providing a method for setting the chemical state of the cells, measured by NMR, in order to draw up with precision the profile (bar code, signature) of the intracellular metabolites specific for the cell type and for the experimental conditions.

The present invention relates to a method for analyzing the chemical state of living cells using nuclear magnetic resonance (NMR) by comparing at least one NMR spectrum and/or at least one NMR measurement value obtained on a sample of said living cells with at least one reference NMR spectrum and/or at least one reference NMR measurement value obtained on at least one reference sample of living cells, so as to identify at least one peak of said NMR spectrum and/or at least one NMR measurement value constituting a marker specific for the metabolic state of said living cells, characterized in that it comprises a step of preparing said sample under conditions which make it possible to set the chemical state of said living cells.

An aim of the invention is also to provide a method for preparing the sample which ensures the stability of the intracellular chemical state from the sampling to the measurement by NMR. Thus, the method according to the invention is characterized in that, in order to prepare said sample, it is subjected to a very low temperature for a sufficient amount of time to stop the intracellular reactions between the moment at which the sample is taken and the moment at which the chemical state of the cells is measured, and optionally also throughout the analysis.

The invention also relates to a method characterized in that the preparation of said sample comprises the following steps:
a) directly and immediately immersing said sample in liquid nitrogen;
b) lyophilizing said sample;
c) optionally storing said sample at very low temperature;
d) at the desired time for the analysis, mixing and redissolving said lyophilized sample, at very low temperature, with a solvent having a very low melting point.

According to a particular embodiment of the invention, the method according to the invention is characterized in that, instead of the liquid nitrogen, a buffered water/methanol mixture at very low temperature is used. According to a preferred embodiment of the invention, the water/methanol mixture is buffered at pH 7.5 and contains 50% of methanol. It is also within the scope of the invention to use other organic compounds in a mixture with the water, which vary by virtue of the nature of the organic compound used, by virtue of the proportion of the organic compound in the mixture, and by virtue of the pH of the mixture. The present invention relates to all the organic compound/water mixtures, and more particularly alcohol/water mixtures, for which the melting point (Mp) is less than 0° C. Among the organic compounds other than an alcohol in a mixture with the water, mention may be made of acetone (Mp=−95° C.) or chloroform (Mp=−64° C.).

According to one embodiment of the invention, the method is characterized in that said solvent is a deuterated water/deuterated methanol mixture and contains 50% of methanol. Similarly, it is also within the scope of the invention to use other types of solvent composed of deuterated water/deuterated organic compound mixtures, and more particularly deuterated water/deuterated alcohol mixtures. The other types of solvent concern all deuterated water/deuterated organic compound mixtures. These mixtures can vary by virtue of the nature of the deuterated organic compound used, by virtue of the proportion of deuterated organic compound in the mixture, or by virtue of the pH of the mixture for example. The melting points of the deuterated solvents differ very little from the equivalent protonated solvents. The solvent most sensitive to deuteration is probably $H_2O$, since the melting point of $D_2O$ is 3.8° C.

According to one embodiment of the invention, the method is characterized in that said very low temperature to which the sample is subjected during its preparation and storage and during the NMR analysis is less than 0° C. Preferably, said very low temperature for preparing and storing the sample is between −10 and −80° C., and more preferably said very low temperature is less than or equal to −80° C. Very preferably, the sample is stored in liquid nitrogen for greater stability. Preferably, said very low temperature throughout the analysis of the sample is between −20° C. and +5° C. such that said temperature is compatible with the use of the rotor and of the probe.

The method for analyzing the chemical state of said cell according to the invention uses NMR with a liquid probe, or NMR with a high resolution HRMAS probe, preferably by two-dimensional HRMAS NMR.

According to a preferred embodiment of the invention, the method according to the invention is characterized in that said living cells are cultured or incubated in a cell or tissue culture medium which contains molecules enriched in stable isotopes. More preferably, said molecules comprise a source of carbon 13 and/or a source of nitrogen 15.

The living cells according to the invention are prokaryotic or eukaryotic, animal or plant, cells. Without drawing up an exhaustive list thereof, examples of living cells according to the invention are given below. Among the prokaryotic cells, mention should be made of blue-green algae, myxobacteria, spirochetes, eubacteria, rickettsias, chlamydia, mycoplasmas and archaebacteria. Among the eubacteria, mention should be made of enterobacteria, such as *Escherichia coli, Bacilli*, such as *Bacillus subtilis, pseuodmonas, campylobacter, rhizobia, argobacteria, azotobacter, micrococci, staphylococci, streptococci*, and *lactobacilli*. Among the cells of eukaryotic microorganisms, mention should be made of green, brown or red algae, fungi such as phycomycetes, ascomycetes, basidiomycetes, and yeast. Among the yeast, mention should be made of *Saccharomyces cerevisiae, Saccharomyces pombe* and *Candida albicans*. Among the animal cells, mention should preferably be made of human cells and cells from mammals, such as bovines, members of the sheep family, members of the goat family, pigs, members of the horse family, and rodents such as mice and rats for example.

The method according to the invention is characterized in that it is used to identify living cells the physiological state of which deviates from the norm. Such a method makes it possible to identify living cells belonging to the group composed for example of cells exhibiting a constitutional or acquired genetic defect and cells subjected to an environmental stress. The term "environmental stress" is intended to denote a physical, chemical or biological agent which causes a reaction of the cell. Among the physical agents, mention should be made, inter alia, of beta-rays, gamma-rays, X-rays, ultraviolet radiation, infrared radiation and visible light. In addition, culturing conditions, which may be aerobic or anaerobic, the pH of the culture medium, which may be acidic, basic or neutral, the concentration of carbon dioxide or of another element in the culture medium, and the temperature constitute physical agents according to the invention. The term "chemical agent" is intended to denote any chemical compound capable of interacting with the cell or one of the membrane-bound cellular components or intracellular components; for example, intercalating agents such as ethidium bromide or propidium iodide constitute chemical compounds according to the invention. The biological compounds of the invention correspond to all compounds capable of causing a cellular biological reaction. Mention may be made, non-exhaustively, of all molecules which interact with a membrane receptor, such as, for example, intracellular communication molecules, hormones, cytokines, lymphokines, interleukins, or antibodies. Viruses also constitute biological agents according to the invention. The biological agents according to the invention also include genetic factors. These genetic factors affect cell metabolism; these factors may be constitutional, such as, for example, in the case of genetic diseases, for instance, Duchenne muscular dystrophy, Steinert myotonic dystrophy, cystic fibrosis, spinal amyotrophy or amyotrophic lateral sclerosis, for example. These factors may be acquired, as in the case of mutations or chromosomal rearrangements, such as a deletion, an insertion, a translocation or a viral integration. According to the invention, said cells exhibiting a constitutional or acquired genetic defect preferably belong to the group of cancer cells, or of human cells from a patient suffering from a constitutional genetic defect, or of cells infected with a virus.

The method according to the invention characterized in that said specific marker is used to screen for chemical or biological molecules.

According to another embodiment of the invention, the method according to the invention is characterized in that it is used to identify an intracellular metabolite specific for a cell type and/or for a cellular metabolic state and/or for cellular environmental conditions.

The method according to the invention can also be used to determine the distribution of intracellular metabolites having an incorporated said stable isotope, for example, carbon 13 or nitrogen 15. The method according to the invention may also be used to qualitatively determine the metabolic pathways responsible for the formation of said metabolites and/or to qualitatively determine the intracellular fluxes generated by the enzymatic catalyst.

The present invention also comprises providing a specific marker which can be obtained using the method according to the invention. An example of a specific marker is given in FIG. 2. The experiment consisted in observing the $^{13}C$ NMR spectrum, with proton decoupling, 10 minutes before and 25 minutes after the passage of a culture of yeast cells under strict aerobic conditions to a culture under anaerobic conditions. Very large variations in intensity, or even the appearance of peaks, are observed, and constitute specific markers. Thus, the signals C1 (55.9 ppm) and C2 (18.0 ppm) for ethanol appear under anaerobic conditions, whereas these signals are not significant on the spectrum of yeast under aerobic conditions. On the other hand, the signal at 91.3 ppm corresponding to the C1 of trehalose almost entirely disappears. Another example of specific markers can be observed in FIG. 5.

Finally, the invention also comprises the use of the NMR spectrum peak or of the NMR measurement value, as identified by implementing the method according to the invention, as a marker of a given metabolic state for screening living cells. The invention therefore also relates to a method for screening living cells, to identify cells exhibiting a given metabolic state, characterized in that the marker according to the invention is used. The invention also relates to the use of the marker according to the invention for screening chemical or biological molecules.

In addition, an object of the invention is also to provide a device coupled to NMR which guarantees the stability of the chemical state throughout the measurement of the chemical state of the biological samples by NMR. The invention therefore relates to a device for implementing the method according to the invention, characterized in that it comprises a superconductor magnet, an electronic console panel, an NMR measuring probe and a refrigeration unit.

The role of the superconductor magnet is to generate a strong magnetic field (up to 18.8 T) which is homogeneous over a sufficiently large volume and the intensity of which is stable over time. The electronic console panel makes it possible to generate high frequency (up to 800 MHz) and very powerful (50 W) pulses and to receive the signals emitted by the sample. The measuring head (European patent EP0856741), marketed by Bruker (article code B1867), receives the sample and transmits the high frequency pulses to it. It also provides detection of the signal emitted. The compound subjected to the measurement is contained in a rotor made of zirconium oxide, 4 mm in diameter. It is introduced into the probe via the top of the magnet using a transfer line (Bruker article code K0219) and comes into position at the centre of a ratio frequency coil in the form of a solenoid. The part containing the coil and the sample is called a stator and has the notable characteristic of being mobile and, by virtue of a pneumatic control unit, of being able to rock such that the axis of the coil, and consequently of the sample, forms an angle of 54.7° relative to the principal magnetic field generated by the magnet (FIG. 1). Once in this position, the turbine is raised and held in levitation by an axial pneumatic stream (bearing) of approximately 1500 mbar entering from the bottom of the rotor. This rotor is hermetically closed by virtue of a KelF cap which has flutes enabling the rotation. This rotation is produced using a second pneumatic stream (drive), the direction of which is tangential relative to the turbine. The drive pressure is approximately 500 mbar and the stream of air hitting the flutes of the cap makes it possible to reach spinning rates of the order of 15000 rev/sec. The bearing and drive pressures, the rocking of the stator and also the ejection of the sample are controlled by a Bruker pneumatic unit (article code H2620).

The 54.7° angle made by the sample with the principal magnetic field is commonly called magic angle. It in fact makes it possible to average the considerable differences in magnetic susceptibility present in samples of living cells. This property makes it possible to obtain NMR signals which are clearly finer than those obtained using conventional high resolution liquid NMR techniques which do not use the concept of magic angle spinning. The technique used is thus known as high resolution magic angle spinning NMR (HR-MAS NMR).

The refrigeration unit, marketed by Bruker under the name BCU05 (article code W1210342), is essential since it makes it possible to considerably slow down, or even freeze, the metabolic processes so as to be able to study, by NMR, the various chemical components inside the cell without their properties being modified during the NMR measurement. This unit cools the dry air stream used to hold the sample in levitation (bearing) to temperatures possibly reaching −20° C., thus ensuring similar temperatures in the region of the sample. This unit functions by means of dry air and makes it possible to generate an air flow rate possibly reaching 2500 l/h. This stream of gas should make it possible for the sample to reach the high spinning rates required for this type of experiment. The flow rate and the temperature of the air should be sufficiently stable to guarantee good stability of the spinning rate and of the temperature in order to prevent the appearance of parasitic artifacts in the NMR spectra. The refrigeration unit connector should be able to withstand considerable pressures while at the same time being sufficiently flexible to be able to be connected easily to the probe and to absorb possible vibrations which might be detrimental to the NMR measurement.

This device is characterized in that it makes it possible to carry out the NMR measurement at a controlled temperature of less than 0° C., preferably between 0 and −20° C.

Other characteristics and advantages of the present invention will be demonstrated more clearly on reading the following examples. In these examples, reference will be made to the following figures:

FIGURES

FIG. 1: General scheme of the device
1. Magic angle: 54.735°
2. Injection and ejection line
3. Spinning gas (drive)
4. Bearing gas (bearing)
5. Shielding
6. Support ceramics
7. RF coil
8. Stator in vertical position to eject the sample
9. Toward tuning circuits
10. Mobile contact
11. Cable for measuring the spinning rate
12. Air for ejection of the sample
13. Support tube
14. Hermetic pivots
15. Tubes used for ejection of the sample
16. Air inlet for vertical positioning
17. Air inlet for positioning at the magic angle
18. Pneumatic piston
19. Micrometer screw for setting the magic angle
20. Dewar
21. Thermocouple
22. Bearing gas inlet
23. Heating resistor FIG. 2: $^{13}$C NMR spectrum with proton decoupling:
under strictly aerobic conditions (bottom)
Experimental conditions: acquisition time 1 s, waiting time 5 s, 350 acquisitions, recording time 30 min, sample spinning rate 1 kHz.
25 minutes after passing from strictly aerobic conditions to anaerobic conditions (top)

Experimental conditions: acquisition time 1 s, waiting time 5s, 639 acquisitions, recording time 53 min, sample spinning rate 1 kHz. The signals characteristic of ethanol are indicated by an asterisk.

Figure 3:
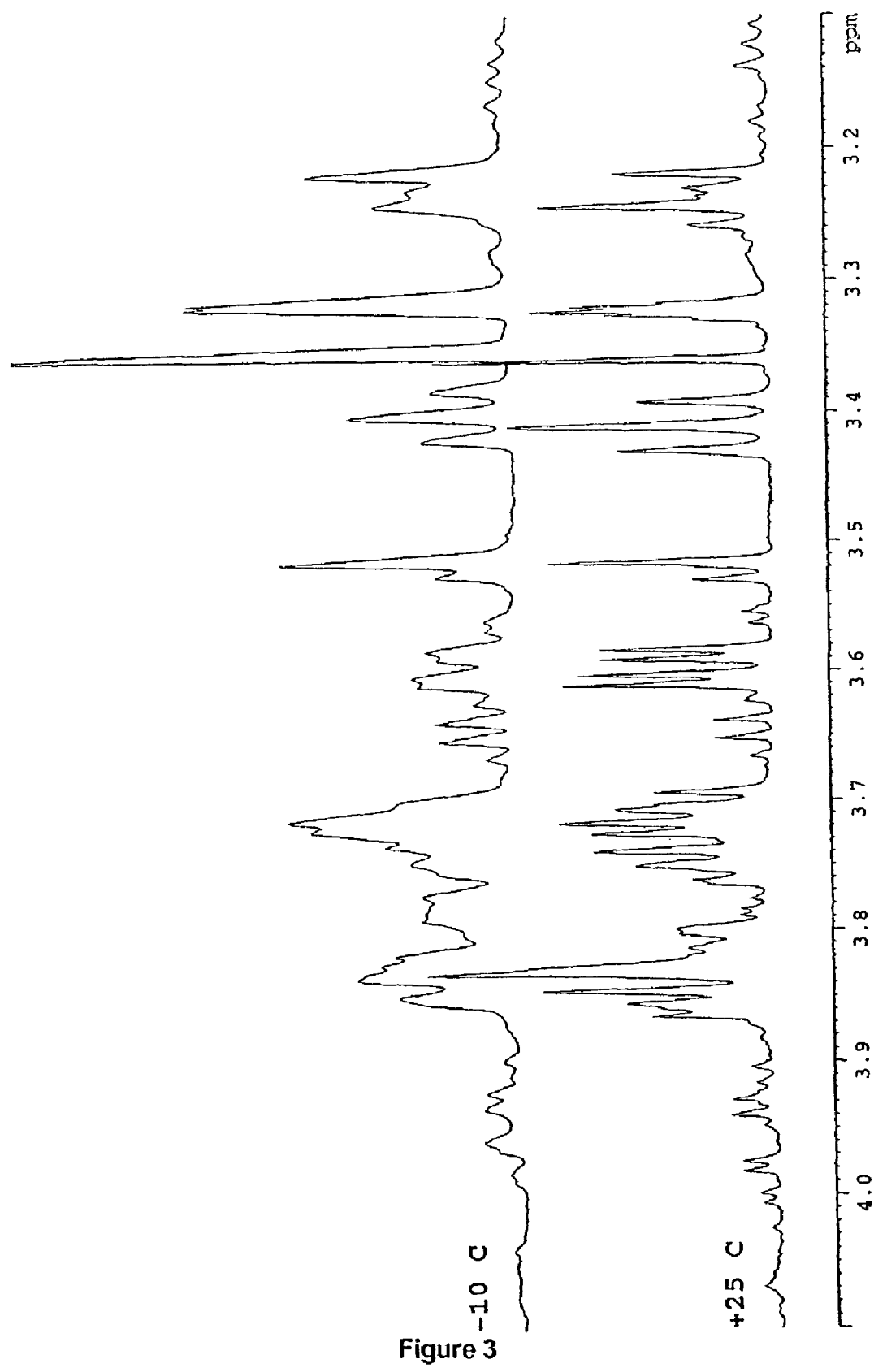

FIG. 3: Influence of temperature on the resolution of the proton spectra produced by HR MAS NMR on yeast The proton spectrum obtained at −10° C. (upper spectrum) shows a resolution which is slightly inferior to that observed on the spectrum obtained at an ambient temperature (+25° C.) (lower spectrum) Experimental conditions: 7 mg of lyophilized cells, solvent 50 μl of methanol-$d_4$;$D_2O$ in a 1:1 volume ratio, acquisition time 1.4 s, presaturation time 0.9 s, 256 acquisitions, recording time 10 min, sample spinning rate 4 kHz. The $D_2O$ contains 0.75% of TSP (trisilyl-$d_4$-propionate acid as chemical shift reference).

Figure 4:
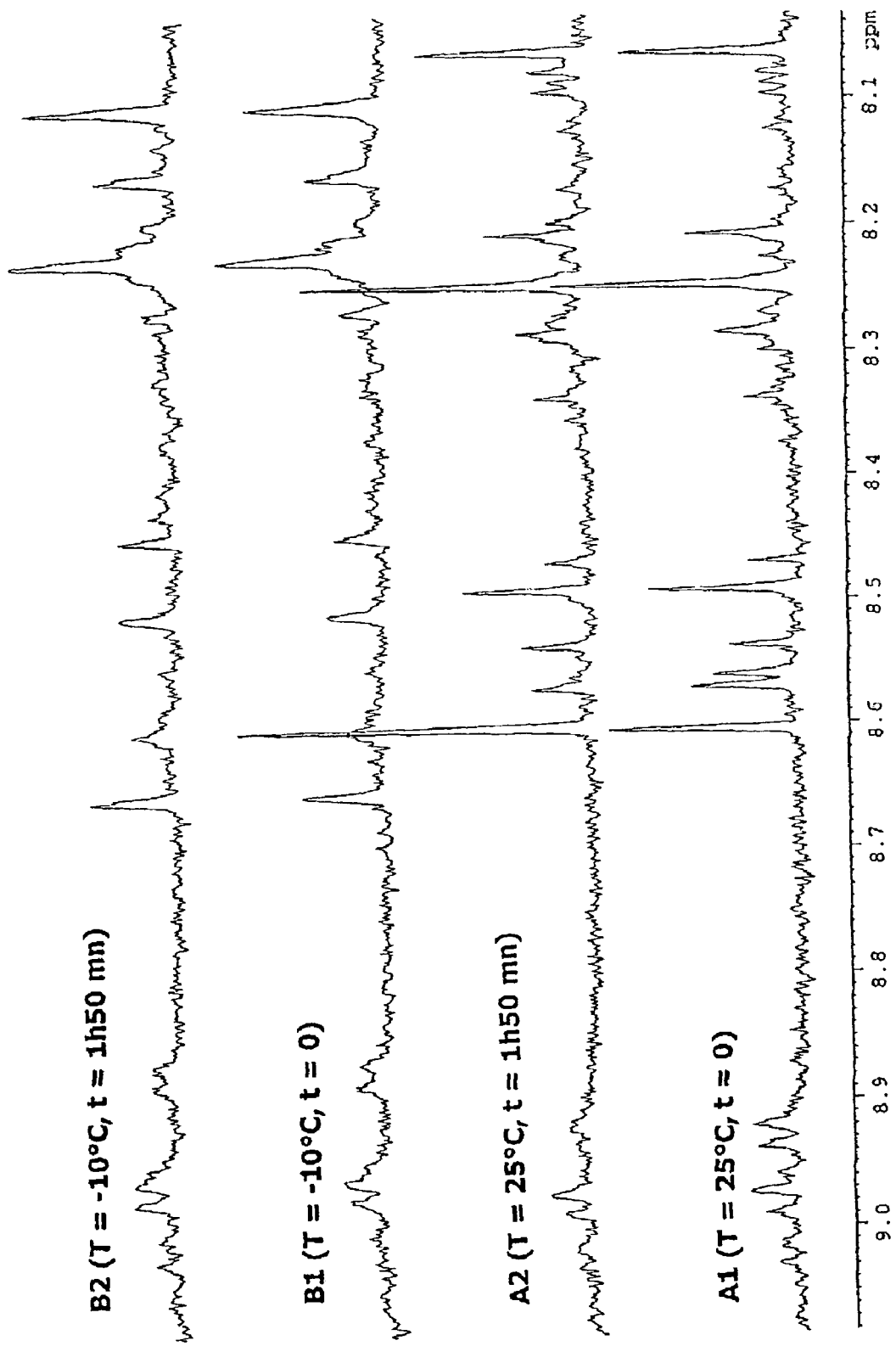

FIG. 4: Influence of temperature on the stability of the proton spectra produced by HR MAS NMR on yeast The conditions for preparing the samples, and for recording the spectra are identical to those of FIG. 3. The experiment was carried out at +25° C. (spectra A1 and A2) and at −10° C. (spectra B1 and B2). The spectra were recorded immediately after preparing the sample and regulating the settings of the spectrometer (spectra A1 and B1), and then after 1 h 50 min under the conditions for NMR data acquisition, keeping the temperature constant (A2 and B2). A much greater stability of the sample is observed, clearly greater at −10° C. than at +25° C. For example, at +25° C., in the region of the spectrum described by the figure, the signals at 8.93, 8.92 and 8.56 ppm disappear almost entirely, whereas the signals at 8.61, 8.10 and 8.08 ppm clearly increase in strength. On the other hand, at −10° C., the variations in strength remain very small over the entire spectrum.

Figure 5:
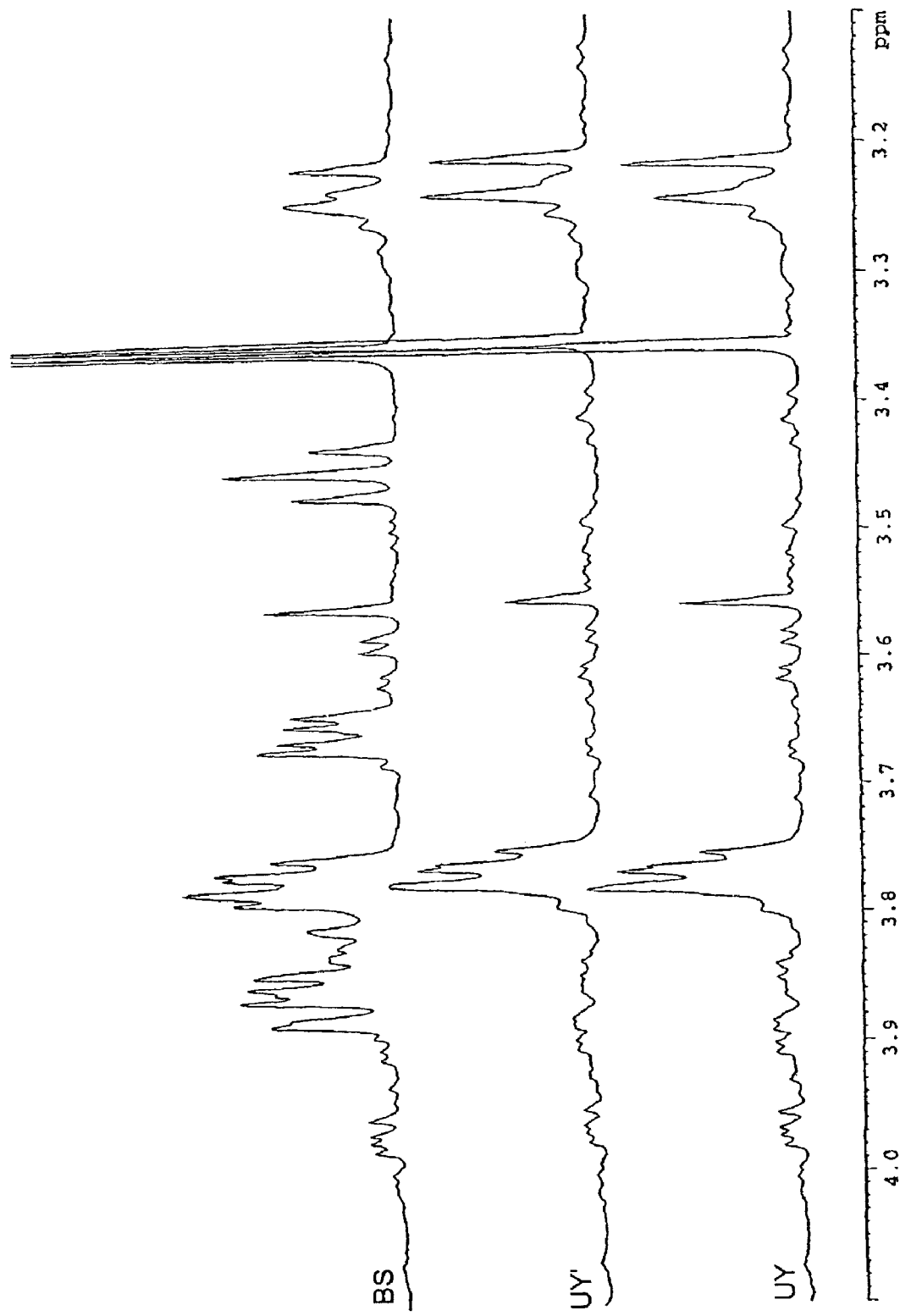

FIG. 5: Characterization of yeast by $^1H$ NMR

The conditions for preparing the samples are identical to those of FIG. 3. Proton spectra for two cultures of ultra yeast (UY and UY') and for a culture of baker's yeast (BS) stopped at the time of total consumption of the glucose (10 g of glucose per liter of culture). This moment is defined by a glucose enzyme assay. The UY and UY' spectra show very good reproducibility of all the experimental steps leading to the recording of the spectra. The spectral differences between UY and BS make it possible to easily distinguish the two yeasts. NMR experimental conditions identical to those of FIG. 3, except T=+2° C. and solvent is 50 μl $D_2O$.

EXAMPLES

1. Materials and Methods

The cells are taken directly from the cell culture and immersed directly in the liquid nitrogen or in a water/methanol mixture (50% by volume) at −40° C. The aim of this step is to stop the intracellular reactions with cold conditions. The temperature gradient imposed on the cells optimizes the rate of heat transfer and results in instantaneous arrest of the intracellular metabolism.

The cells are then centrifuged. The cell pellet is rinsed twice with PBS (phosphate buffer saline), and then centrifuged a final time. The cells are then lyophilized and stored at −80° C.

The sample to be measured is prepared by mixing, directly at 0° C., in the sample-carrier rotor, 7 mg of lyophilized cells with a solution of 50 μl of a mixture of deuterated methanol and deuterated water in a 1:1 volume ratio and containing 0.375% of TSP as chemical shift reference. After vortexing for 10 seconds to homogenize the sample, the rotor is placed in a bath of crushed ice and is ready for NMR analysis. The spectrum is recorded after setting the rotor to spin, stabilizing the temperature of the sample, tuning the measuring head and optimizing the homogeneity of the magnetic field $B_0$. The time taken to regulate all these settings should not exceed 5 min.

2. Results

FIG. 3 shows that the resolution of the spectra is slightly inferior at low temperature. This resolution remains, however, very acceptable for the analysis and interpretation of HRMAS NMR spectra obtained in this way.

FIG. 4 shows that the sample is clearly more stable at low temperature. This result shows that the spectra recorded at −10° C. give a much truer image of the cellular state to be examined than the spectra obtained at ambient temperature. The method, which blocks the cellular state by decreasing the temperature, therefore makes it possible to notably improve the sensitivity of the measurement by making it possible to increase the acquisition time for the NMR spectra. Freezing the state of the biological systems to be studied then provides the possibility of recording two-dimensional NMR experiments (2D NMR). These experiments, of the homonuclear type (for example: COSY, TOCSY, NOESY) or heteronuclear type (for example: $^1H$—$^{13}C$ or $^1H$—$^{15}N$ reverse correlation of the HSQC, HMQC and/or HMBC type), make it possible to provide structural and dynamic information regarding the metabolites studied. In addition, 2D NMR makes it possible to very clearly increase the resolution due, in particular, to the spectral dispersion over the second dimension.

Figure 2:
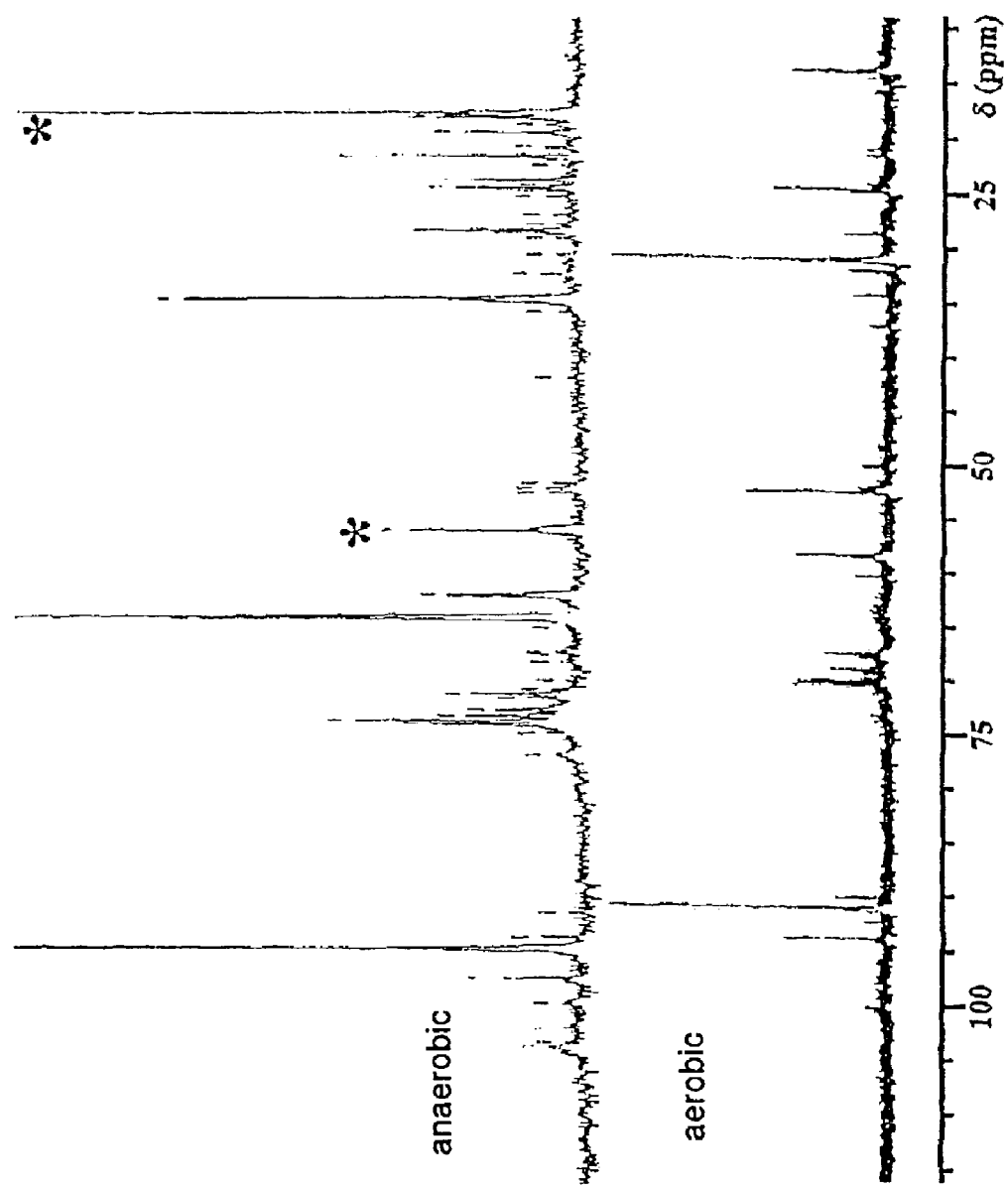

FIGS. 2 and 5 show the possibility of characterizing a cell culture in a few minutes. By comparison to a databank, cell samples can be characterized by their type (FIG. 5) or their culture conditions (FIG. 2). These examples can readily be extended to other variations in cell culture (culture medium, pH, temperature, sample time) and to genetic differences which affect the metabolic network (mutations).

REFERENCES

Cameron et al. (1977) Curr. Opin. Biotechnol. 8: 175-80.
De Koning et al.(1992) Anal Biochem. 204: 118-123.
Gadian et al. (1983) Oxford University Press (Eds), Oxford, UK.
Gancedo et al. (1973) Biochimie 55: 205-211.
Gonzalez et al. (1997) Yeast 13: 1347-1356.
Jeffrey et al. (1991) Trends Biochem. Sci. 16: 5-10.
Middleton et al. (1998) Magn Reson Med. 40: 166-169.
Ryll et al. (1991) J Chromatogr. 570: 77-88.
Seiler et al. (1994) Institute of Biotechnology, ETH, Zurich.
Teusink et al. (1998) J. Bacteriol. 180: 556-562.
Theobald et al. (1996) Biotechnology Techniques. 10: 297-302.
Weuster-Botz et al. (1996) Ad. Biochem. Eng. Biotechn. 34: 75-108.

The invention of claimed is:

1. A method for preparing a sample and for analyzing the chemical state of living cells by nuclear magnetic resonance (NMR) comprising:
i) preparing a sample of living cells so as to set the chemical state of the cells by:
a) subjecting said sample of living cells to a temperature at or lower than −80° C. so as to stop intracellular reactions, by directly immersing said sample in liquid nitrogen, followed by,
b) lyophilizing said sample;
ii) storing said sample at said temperature less than or equal to −80° C.

iii) just before performing the NMR analysis, mixing and redissolving said lyophilized sample, at a temperature between 0° C. and −20° C., with a solvent having a very low melting point and being liquid at the temperature between 0° C. and −20° C.;

iv) obtaining, at the temperature between 0° C. and −20° C., at least one NMR spectrum and/or at least one NMR measurement value through High Resolution Magic Angle Spinninig (HRMAS) NMR; and v) comparing said at least one HRMAS NMR spectrum and/or at least one HRMAS NMR measurement value with at least one reference NMR spectrum and/or at least one reference NMR measurement value obtained on at least one reference sample of living cells.

2. The method of claim 1, wherein said sample of living cell is taken from a cell or tissue culture medium which contains molecules enriched in stable isotopes, in which said living cells are cultured or incubated.

3. The method of claim 2, wherein said molecules comprise a source of carbon 13 and/or a source of nitrogen 15.

4. The method of claim 1, wherein said living cells are selected among the group consisting of prokaryotic, eukaryotic, animal and plant cells.

5. The method of claim 1, wherein at least one peak of said NMR spectrum and/or at least one NMR measurement value is identified to constitute a marker specific for the metabolic state of said living cells.

6. The method of claim 1, wherein living cells which physiological state deviates from a norm are identified.

7. The method of claim 6, wherein said identified living cells are selected among the group consisting of cells exhibiting a constitutional or acquired genetic defect and cells subjected to an environmental stress.

8. The method of claim 7, wherein said cells exhibiting a genetic defect are selected among the group consisting of cancer cells and cells infected with a virus.

9. The method of claim 1, wherein an intracellular metabolite specific for a cell type and/or for a cellular metabolic state and/or for cellular environmental conditions is identified.

10. The method of claim 9, comprising determining the distribution of intracellular metabolites having incorporated a stable isotope; and/or quantitatively determining the metabolic pathways responsible for the formation of said metabolite; and/or quantitatively determining the intracellular fluxes generated by enzymatic catalysis.

11. The method of claim 1, further comprising using magic angle spinning to averaging magnetic susceptibility differences.

12. The method of claim 1, further comprising identifying an intracellular metabolite specific for a cell type and/or for a cellular metabolic state and/or for cellular environmental conditions.

13. A method for preparing a sample and for analyzing the chemical state of living cells by nuclear magnetic resonance (NMR) comprising:
   i) preparing a sample of living cells so as to set the chemical state of the cells by:
       a) subjecting said sample of living cells to a temperature at or lower than −80° C. so as to stop intracellular reactions, by directly immersing said sample in liquid nitrogen, followed by,
       b) lyophilizing said sample;
   ii) storing said sample at said temperature less than or equal to −80° C.;
   iii) just before performing the NMR analysis, mixing and redissolving said lyophilized sample, at a temperature between 0° C. and −20° C., with a solvent having a very low melting point and being liquid at the temperature between 0° C. and −20° C.;
   iv) obtaining, at the temperature between 0° C. and −20° C., and without further extraction of metabolites, at least one NMR spectrum and/or at least one NMR measurement value through High Resolution Magic Angle Spinninig (HRMAS) NMR; and
   v) comparing said at least one HRMAS NMR spectrum and/or at least one HRMAS NMR measurement value with at least one reference NMR spectrum and/or at least one reference NMR measurement value obtained on at least one reference sample of living cells.

14. The method of claim 13, further comprising using magic angle spinning to averaging magnetic susceptibility differences.

15. The method of claim 13, further comprising identifying an intracellular metabolite specific for a cell type and/or for a cellular metabolic state and/or for cellular environmental conditions.

* * * * *